United States Patent
Kim et al.

(10) Patent No.: US 9,180,171 B2
(45) Date of Patent: Nov. 10, 2015

(54) METHOD OF REGULATING FERTILIZING ABILITY USING CYCLIC ADP-RIBOSE AND CD38

(71) Applicant: Industrial Cooperation Foundation Chonbuk National University, Jeonju-si, Jeollabuk-do (KR)

(72) Inventors: Uh-Hyun Kim, Jeonju-si (KR); Kwang-Hyun Park, Jeonju-si (KR); Byung-Ju Kim, Jeonju-si (KR)

(73) Assignee: Industrial Cooperation Foundation Chonbuk National University, Jeollabuk-Do (KR)

( * ) Notice: Subject to any disclaimer, the term of this patent is extended or adjusted under 35 U.S.C. 154(b) by 0 days.

(21) Appl. No.: 13/783,828

(22) Filed: Mar. 4, 2013

(65) Prior Publication Data

US 2013/0224177 A1    Aug. 29, 2013

Related U.S. Application Data

(62) Division of application No. 13/357,782, filed on Jan. 25, 2012, now abandoned.

(60) Provisional application No. 61/436,050, filed on Jan. 25, 2011.

(51) Int. Cl.
```
A61K 38/47    (2006.01)
A61K 31/7076  (2006.01)
A61K 31/00    (2006.01)
A61K 31/57    (2006.01)
A61K 31/708   (2006.01)
```

(52) U.S. Cl.
CPC ............. *A61K 38/47* (2013.01); *A61K 31/00* (2013.01); *A61K 31/57* (2013.01); *A61K 31/708* (2013.01); *A61K 31/7076* (2013.01)

(58) Field of Classification Search
None
See application file for complete search history.

(56) References Cited

PUBLICATIONS

Kramer et al., High Expression of a CD38-Like Molecllie in Normal Prostatic Epithelillm and its Differential Loss in Benign and Malignant Disease, The Journal of Urology, 1995, vol. 154, pp. 1636-1641.*
Melendrez et al., Comparison of the Ability of Progesterone and Heat Solubilized Porcine Zona Pellucida to Initiate the Porcine Sperm Acrosome Reaction In Vitro, Molecular Reproduction and Development, 1994, vol. 39, pp. 433-438.*
Fabiani et al., Prolongation and improvement of prostasome promotive sperm forward motility, European Journal of Obstetrics & Gynocology and Reproductive Biology, 1995, vol. 58, pp. 191-198
Ronquist et al., The Prostate, 2012, vol. 72, pp. 1736-1745.*
Ronquist et al., ProstasomesAreHeterogeneous Regarding Size andAppearance but Affiliated to oneDNA-Containing Exosome Family, The Prostate, 2012, vol. 72, pp. 1736-1745.*
Clementi et al., "The Type 2 Ryanodine Receptor of Neurosecretory PC12 Cells is Activated by Cyclic ADP-ribose". Journal of Biological Chemistry. 1996; 271(30): 17739-17745.
Arienti, Giuseppe et al., "The motility of human spermatozoa as influenced by prostasomes at various pH levels", Biology of a Cell, 91 (1999) pp. 51-54.
Lefievre et al., "Communication between female tract and sperm", Communicative & Integrative Biology vol. 2: Issue 2, pp. 82-85, Mar./Apr. 2009.
Dejian Ren & Jingsheng Xia, "Calcium Signaling Through CatSper Channels in Mammalian Fertilization", Physiology 25: 165-175, 2010.
Park et al., "$Ca^{2+}$ Signaling Tools Acquired from Prostasomes Are Required for Progesterone-Induced Sperm Motility", Science Signaling vol. 4 Issue 173, May 17, 2011.

* cited by examiner

*Primary Examiner* — Thane Underdahl
*Assistant Examiner* — Christopher Keller
(74) *Attorney, Agent, or Firm* — Cesari and McKenna, LLP

(57) ABSTRACT

The present invention relates to a pharmaceutical composition for promoting fertilization comprising cyclic ADP-ribose or its derivative, CD38 and to a method of promoting fertilization by promoting the synthesis of cyclic ADP-ribose to increase sperm motility. Also, the present invention relates to a pharmaceutical composition for contraception and a method for inhibiting fertilization, which can inhibit the expression or function of cyclic ADP-ribose to reduce sperm motility, thereby inhibiting fertilization.

4 Claims, 8 Drawing Sheets

METHOD OF REGULATING FERTILIZING ABILITY USING CYCLIC ADP-RIBOSE AND CD38

CROSS REFERENCE TO RELATED APPLICATIONS

This application is a division of U.S. application Ser. No. 13/357,782, filed Jan. 25, 2012 and claims the benefit of U.S. Application No. 61/436,050, filed Jan. 25, 2011. The contents of the foregoing applications are incorporated herein by reference.

BACKGROUND OF THE INVENTION

1. Field of the Invention

The present invention relates to a pharmaceutical composition for promoting fertilization comprising cyclic ADP-ribose or its derivative. More specifically, the present invention relates to a pharmaceutical composition for promoting fertilization and a method for promoting fertilization, which can increase sperm motility using cyclic ADP-ribose and CD38, thereby promoting fertilization.

Also, the present invention relates to a pharmaceutical composition for contraception comprising an antagonist of cyclic ADP-ribose. More specifically, the present invention relates to a pharmaceutical composition for contraception and a method for inhibiting fertilization, which can inhibit a pattern of a continuous increase in calcium caused by progesterone to inhibit sperm motility, thereby inhibiting fertilization.

2. Description of the Prior Art

Spermatozoa are produced in the testis and undergo post-gonadal modifications in the epididymis to acquire fertilizing ability. In epididymal plasma, high-molecular-weight proteins and such small molecules as free carnitine convert the gametes into competent and functional cells. Free L-carnitine is taken up from blood plasma and concentrated in the epididymal lumen. This epididymal secretion is beneficial for spermatozoa and is not merely an excretory waste. Free carnitine goes through the sperm plasma membrane by passive diffusion. Free L-carnitine is acetylated in mature spermatozoa only. The excess acetyl-CoA from the mitochondria is probably stored as acetyl-L-carnitine and modulates the reserves of free CoA essential to the function of the tricarboxylic acid cycle. This property of L-carnitine of buffering CoA in the mitochondrial matrix is known in somatic cells but is accentuated in male germinal cells. The relationship between the endogenous pool of free and acetylated L-carnitine and the percentage of progressive sperm motility indicates a more important metabolic function. Thus, the potential of initiating sperm motility which takes place in the epididymis is probably independent of the carnitine system while the energy properties of acetyl-L-carnitine is relevant in situations of "energy crisis". The uptake of cytoplasmic free L-carnitine in mature spermatozoa must be a protective form of mitochondrial metabolism useful to the survival of this isolated cell.

Idiopathic asthenozoospermia, a disorder of sperm motility, is illustrative of certain conditions in this area. It is a post-testicular cause of infertility due to various ethiology, i.e. congenital defects of the sperm tail, maturation defects, immunological disorders or infection. Several drugs for treating idiopathic asthenozoospermia, none of them completely satisfactory, are known.

Antiestrogen drugs (such as clomiphene citrate and tamoxifen) block sex hormones from inhibiting the Follicle Stimulating Hormone (FSH) and the Luteinizing Hormone (LH) in the brain. This triggers an increased release of LH and FSH, which in turn stimulates testosterone production. Increased testosterone level improves spermatogenesis, thus improving sperm density and motility. However, a recent randomized, double-blind, multicenter study of 190 couples by the World Health Organization (WHO) showed no effect of clomiphene citrate. Tamoxifen was claimed to improve sperm concentration but no change in motility was usually detected. As for clomiphene, recent studies did not confirm its efficacy. Testolactone, an aromatase inhibitor, prevents the conversion of testosterone to estradiol. It has been tested in patients with idiopathic oligospermia but contrasting results have raised many doubts on its efficacy. Mesterolone is a synthetic androgen widely used to treat idiopathic male infertility. A recent study sponsored by WHO failed to show any efficacy of this drug. Thus, studies on a method of promoting fertilizing ability by increasing sperm motility are urgently required.

Calcium signaling in sperm is known to be released from the calcium store present in the midpiece and plays an important role in sperm motility, and calcium signaling by progesterone was reported to occur through a new mechanism having no concern with $IP_3$ that is a general calcium signal initiation site (Fabiani et al., Hum. Reprod, 9, 1485 (1994)). Furthermore, it is known that calcium signaling occurring in many cells stimulates RyR, which opens the calcium store by cyclic ADP-ribose, to release calcium into the cytoplasm, but specific mechanisms in sperm and sperm motility have not yet been reported (Arienti et al., Biol. Cell. 91, 51-54 (1999); Harper et al., J. Biol. Chem. 279, 46315-46325 (2004); Mészáros, Nature 364, 76-79 (1993)). However, it is known that sperm has no endoplasmic reticulum, unlike other cells, and SERCA that is an important calcium channel in the intracellular calcium store is not present in sperm, and secretory pathway $Ca^{2+}$-ATPase is present in place of SERCA (Clapham, Cell 131, 1047-1058 (2007)).

CD38, a cell membrane protein, uses intracellular NAD as a substrate to synthesize cyclic ADP-ribose (cADPR) and nicotinic acid adenine dinucletide phosphate (NAADP), which release calcium from intracellular calcium store into the cytoplasm, thereby controlling the various functions of cells (Berridge et al., Nat. Rev. Mol. Cell Biol. 4, 517-529 (2003); Lee H C, Mol. Med. 12, 317-323 (2006)). Also, it was reported that CD38 binds specifically to CD31 present on the surface of other cells so as to perform intracellular signaling (Deaglio et al., Immunol. 1997; 160:395-402).

The mammalian sperm contains granules having a size of several ten to several hundred nanometers, which are prostasomes secreted from the prostate. The prostasomes bind specifically to spermatozoa under weakly acidic conditions similar to the internal conditions of the female vagina, resulting in structural or functional changes (Ronquist and Brody, Biochim. Biophys. Acta 822, 203-218 (1985); Arienti et al., Membr. Biol. 155, 89-94 (1997); Publicover et al., Nat. Cell Biol. 9, 235-242 (2007); Burden et al., Hum. Reprod. Update 12, 283-292 (2006)). The binding of prostasomes to spermatozoa is known to increase sperm motility (Fabiani et al., Hum. Reprod. 9, 1485-1489 (1994); Arienti et al., Biol. Cell 91, 51-54 (1999)), and it was reported that the intracellular calcium content of spermatozoa bound to prostasomes was increased (Arienti et al., Biol. Cell 91, 51-54 (1999)), but a mechanism which is involved in calcium release by prostasomes has not yet been known. The results of analysis of prostasomes by proteomics techniques indicated the presence of several hundred proteins, including CD38 that is the typical enzyme of ADP-ribosyl cyclase (Palmerini et al., Cell Calcium 25, 291-296 (1999)), but the functional role of the proteins or the correlation of the proteins with other molecules has not yet been elucidated.

It has been reported that prostasomes present in sperm contain various proteins, including CD38 (Palmerini et al., Cell Calcium 25, 291-296 (1999)), and it was reported that a protein group important in the signaling pathway of cyclic SDP-ribose synthesized by CD38 is transferred into spermatozoa (Park et al., Science Signaling, 4, 31-41 (2011)), in which the protein group typically includes progesterone receptor, vacuolar-type $H^+$-ATPase, ryanodine receptor, secretory pathway $Ca^{2+}$-ATPase, and novel ADP-ribosyl cyclase different from CD38.

Thus, it is needed to find the relationship between prostasomes and sperm motility and find a substance that regulates sperm motility. Also, a new study on a method capable of regulating fertilizing ability by regulating sperm motility based on these findings is required.

SUMMARY OF THE INVENTION

It is an object of the present invention to provide a composition and method of regulating fertilizing ability by regulating sperm motility. More specifically, according to the present invention, sperm motility can be regulated using cyclic ADP-ribose and CD38, thereby effectively promoting fertilization or inducing contraception as desired.

The present invention provides a pharmaceutical composition for promoting fertilization comprising cyclic ADP-ribose or its derivative.

The present invention provides a pharmaceutical composition for promoting fertilization comprising CD38.

The present invention provides a method of promoting fertilization by increasing sperm motility, the method comprising a step of promoting the synthesis of cyclic ADP-ribose.

The present invention also provides a pharmaceutical composition for contraception comprising an antagonist of cyclic ADP-ribose.

The present invention also provides a method for inhibiting fertilization comprising the expression of cyclic ADP-ribose.

BRIEF DESCRIPTION OF THE DRAWINGS

In FIG. 1, A: the results of Western blot of CD38 in sperm (lane 1) and prostasome (lane 2); B: the results of analyzing cGDPR formation, the typical activity of intracellular ADP-ribosyl cyclase, in prostasome-bound sperm or prostasome-unbound sperm; C: the results of analyzing the effect of pH on the binding of prostasome to sperm; D: results indicating that the binding of prostasome to sperm is site-specific to the midpiece; E: the results of examining the formation of intracellular cyclic ADP-ribose and nicotinic acid adenine dinucletide phosphate as a function of time in prostasome-bound sperm or prostasome-unbound sperm.

In FIG. 2, A (left): the distribution of calcium signals by progesterone according to the locations (acrosome, midpiece and principal piece); A (right): a schematic diagram of sperm and the locations where calcium signals are measured; B: changes in calcium signals in the midpiece by progesterone according to the presence or absence of extracellular calcium in prostasome-unbound sperm; C: changes in calcium signals in the midpiece by progesterone according to the presence or absence of extracellular calcium in prostasome-bound sperm; D: changes in calcium signals in the midpiece by progesterone after pretreatment of prostasome-bound sperm with 8-Br-cADPR that is an antagonist of cyclic ADP-ribose.

DETAILED DESCRIPTION OF THE INVENTION

Figure 1:
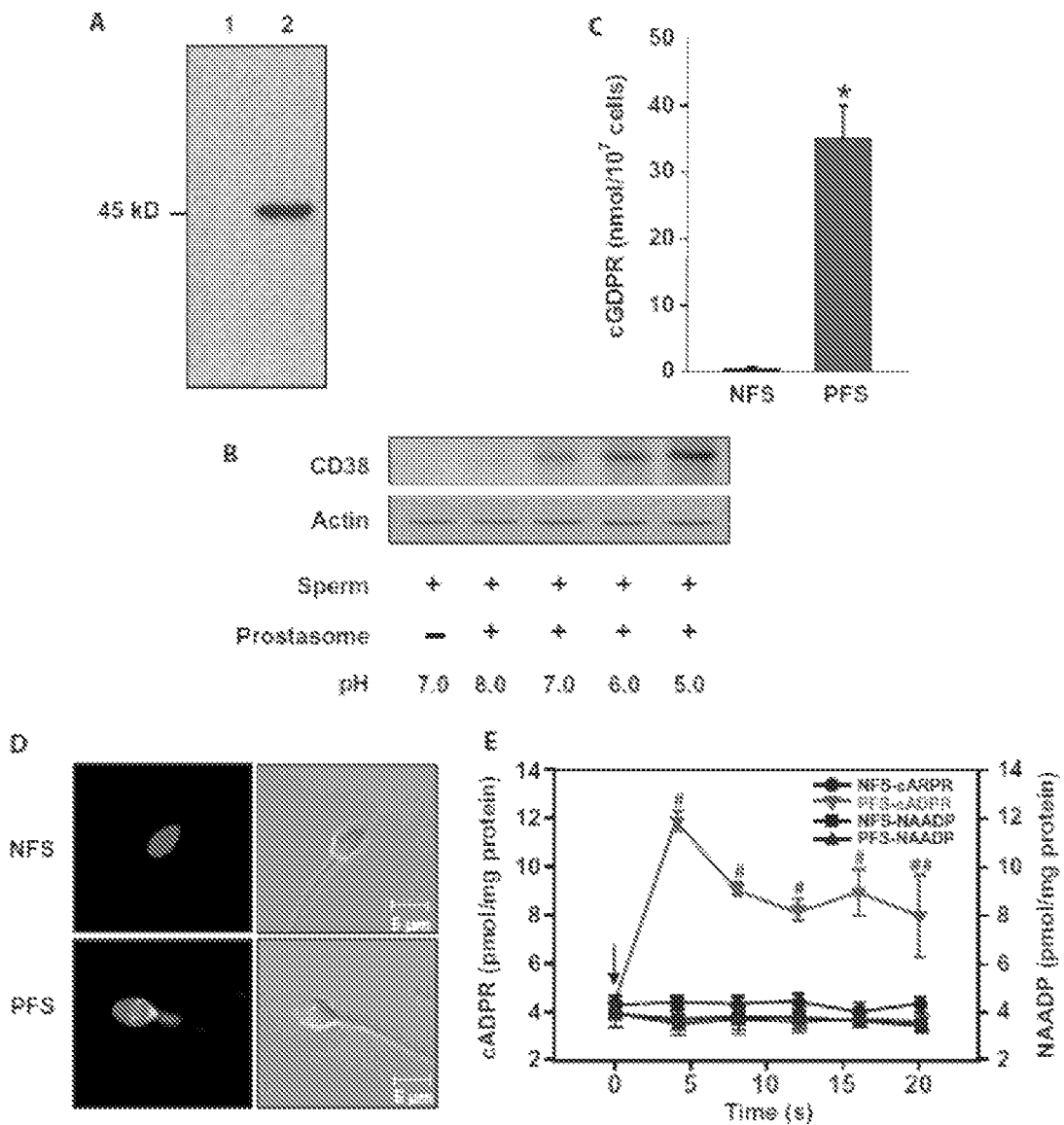
FIG. 1 shows that ADP-ribosyl cyclase (hereinafter referred to as CD38) contained in prostasome is transferred to the midpiece of sperm to catalyze the synthesis of cyclic ADP-ribose by progesterone in cells.

The present invention relates to a pharmaceutical composition for promoting fertilization comprising cyclic ADP-ribose or its derivative.

The present invention provides a pharmaceutical composition for promoting fertilization comprising CD38.

The pharmaceutical composition according to the present invention may additionally comprise a pharmaceutically acceptable salt.

In the present invention, the pharmaceutically acceptable salt means a salt which is conventionally used in the medical field, and examples thereof include, but are not limited to, inorganic ionic salts of calcium, potassium, sodium and magnesium, inorganic acid salts of hydrochloric acid, nitric acid, phosphoric acid, hydrobromic acid, iodic acid, tartaric acid and sulfuric acid, salts of inorganic acids such as acetic acid, trifluoroacetic acid, citric acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanilic acid, hydroiodic acid, mandelic acid, malic acid, nitric acid, palmic acid, panthtenic acid, succinic acid and tartaric acid, salts of sulfonic acids such as methanesulfonic acid, ethanesulfonic acid, benzenesulfonic acid, p-toluenesulfonic acid, camphorsulfonic acid or naphthalenesulfonic acid, salts of amino acids such as glycine, arginine and lysine, and salts of amines such as trimethylamine, triethylamine, ammonia, pyridine and picoline. For example, the pharmaceutically acceptable salt may be a salt of an inorganic acid such as hydrochloric acid, or a salt of an organic acid such as methanesulfonic acid.

The pharmaceutical composition of the present invention may be administered orally or parenterally (e.g., intravenous, subcutaneous, intraabdominal or topical routes). The dose of the pharmaceutical composition of the present invention may vary depending on the patient's weight, age, sex and physical condition, diet, the mode of administration, the administration period or interval, excretion rate, constitutional specificity, the property of the formulation, the severity of the disease, etc.

For administration, the pharmaceutical composition may be formulated into various forms. The pharmaceutical composition may be formulated into various forms with a carrier. The carrier is a solid, semi-solid or liquid formulation adjuvant that is nontoxic, inert and pharmaceutically acceptable, and examples thereof include fillers, extenders, binders, wetting agents, disintegrants, dispersants, surfactants or diluents.

The pharmaceutical composition of the present invention may be formulated in a unit dosage form. For example, the formulated dosage unit may comprise 1, 2, 3 or 4 times or ½, ⅓ or ¼ times the daily dose of the active compound. Preferably, the individual dosage includes a one-time dose of the active compound, which generally corresponds to all, ½, ⅓ or ¼ of the daily dose.

The pharmaceutical composition of the present invention may be formulated into tablets, coated tablets, capsules, pills, granules, suppositories, liquids, suspensions, emulsions, pastes, ointments, gels, creams, powders or sprays. For example, for oral administration, the pharmaceutical composition may be formulated into solid formulations such as tablets, pills, powders, granules or capsules, or liquid formulations such as suspensions, solutions, emulsions or syrups. For parenteral administration, the pharmaceutical composition may be formulated into injectable solutions, suspensions, emulsions, freeze-dried agents or suppositories.

The present invention relates to a method of promoting fertilization by increasing sperm motility, the method comprising promoting the synthesis of cyclic ADP-ribose. In the present invention, cyclic ADP-ribose can be synthesized in protasome-bound sperm.

For the binding of protasome to sperm, protasome and a sperm protein may be mixed at a ratio of 5:1 to 2:1, and preferably 2:1.

The present invention may comprise treating protasome-bound sperm with progesterone in order to promote the fertilization of sperm. Treatment with progesterone enables sperm motility to be increased by 2 times or more, the release of calcium in cells to occur and calcium to be increased for a long time.

Also, the present invention may provide a pharmaceutical composition and method for contraception, which can be used to inhibit the expression and function of cyclic ADP-ribose to reduce sperm motility.

More specifically, in the present invention, any material that can inhibit the expression of cyclic ADP-ribose gene may be used without limitation. More specifically, siRNA, antisense RNA, shRNA, or aptamers may be used. Also, antibodies, antagonists or neutralizing proteins may be used to inhibit the function of cyclic ADP-ribose. More specifically, 8-Br-cADPR or 8-amino-cADPR may be used as an antagonist for inhibiting the sperm motility of cyclic ADP-ribose.

The present invention also provides a pharmaceutical composition and method for contraception, which can use the antagonist to inhibit the expression of cyclic ADP-ribose and inhibit a continuous calcium increase pattern by progesterone, thereby reducing fertilization possibility.

Hereinafter, the present invention will be described in detail with reference to preferred examples. It is to be understood, however, that these examples are provided for a better understanding of the present invention and are not intended to limit the scope of the present invention.

Example 1

Isolation of Protasome

The isolation of protasome was performed using a modification of the method of Palmerini et al. (Palmerini et al., Fertil. Steril. 80, 1181-1184 (2003)). The human semen was taken and 4-fold diluted with Tris buffered saline (TBS: 30 mM Tris, pH 7.4, 130 mM NaCl), and the dilution was centrifuged at 3,000 rpm for 30 minutes to collect the supernatant. The supernatant was centrifuged using a high-speed centrifuge (Beckman) at 15,000×g for 20 minutes, and then the supernatant was centrifuged using a ultra-high speed centrifuge at 105,000×g for 2 hours, and the precipitate was collected. The collected precipitate was resuspended in the same buffer, and a fraction which was first eluted using Sephadex G-200 (Sigma, USA) was taken, centrifuged and then suspended.

Example 2

Isolation of Sperm

In order to isolate protasome-unbound sperm, ejaculated semen was immediately 20-fold diluted with 1% BSA-containing Bigger, Whitten, and Whittingham (BWW) medium [10 mM Hepes, 20 mM sodium lactate, 5 mM glucose, 0.25 mM sodium pyruvate, penicillin G (80 mg/liter), streptomycin sulfate (50 mg/liter), 95 mM NaCl, 4.8 mM KCl, 1.3 mM $CaCl_2$, 1.2 mM $KH_2PO_4$, and 1.2 mM $MgSO_4$ in 25 mM $NaHCO_3$ buffer, pH 7.4] preheated to 37° C. The dilution was centrifuged at 900×g for 20 minutes, and the precipitate was washed twice with the same buffer.

Example 3

Binding of Prostasome to Sperm

The isolated sperm were diluted with a weakly alkaline buffer or fusion buffer (150 mM NaCl, 1 mM $CaCl_2$, 1 mM $MgCl_2$, 5 mM glucose with either 2 mM Hepes (pH 8.0) or 20 mM MES (pH 5.0, fusion buffer)) containing 0.32 M sucrose. The dilution was mixed with prostasome such that the ratio of prostasome:sperm protein was 2:1. The mixture was allowed to react at 37° C. for 15 minutes. The reaction product was centrifuged at 600×g for 10 minutes, and the precipitate was collected, resuspended in BWW buffer and used in the experiment.

As a result, as can be seen in FIG. 1, the sperm had little or no ADP-ribosyl cyclase (hereinafter referred to as CD38), but the prostasome contained a large amount of CD38. The formation of cGDPR (the typical enzymatic activity of CD38) in the prostasome-unbound sperm and the prostasome-bound sperm was measured, and as a result, it could be seen that the prostasome-bound sperm had very high CD38 activity. Also, the binding of prostasome was the highest at a pH of 5.0 similar to the internal acidity of the female vagina and decreased toward alkaline pH values. The prostasome was bound specifically to the midpiece of sperm, as demonstrated by detecting CD38 using an immune staining method. In order to examine the formation of cyclic ADP-ribose and nicotinic acid adenine dinucletide phosphate which are typical metabolites of CD38, the sperm to which prostasome was unbound or bound was treated with progesterone, after which the level of each molecule in the sperm was measured at varying points of time. As a result, it could be seen that the synthesis of cyclic ADP-ribose rapidly increased only in the prostasome-bound sperm within several seconds and did not increase in other groups. Also, nicotinic acid adenine dinucletide phosphate was not formed in any of the groups, suggesting that the signaling of sperm by progesterone has no connection with nicotinic acid adenine dinucletide phosphate.

Example 4

Measurement of Calcium in Sperm Cells

In order to measure intracellular calcium release, the sperm suspension pretreated with fluo-3 (molecular probe, USA) was titrated in a confocal dish (SPL, Seoul, Korea) coated with poly-L-lysine (Sigma-Aldrich, USA) and was allowed to react in a $CO_2$ incubator for 20 minutes to attach the cells. Calcium in the cells was measured by a confocal microscopy system (Nikon) using the method of Tsien et al. (Tsien et al., Nature 295, 68-71 (1982)).

Figure 2:
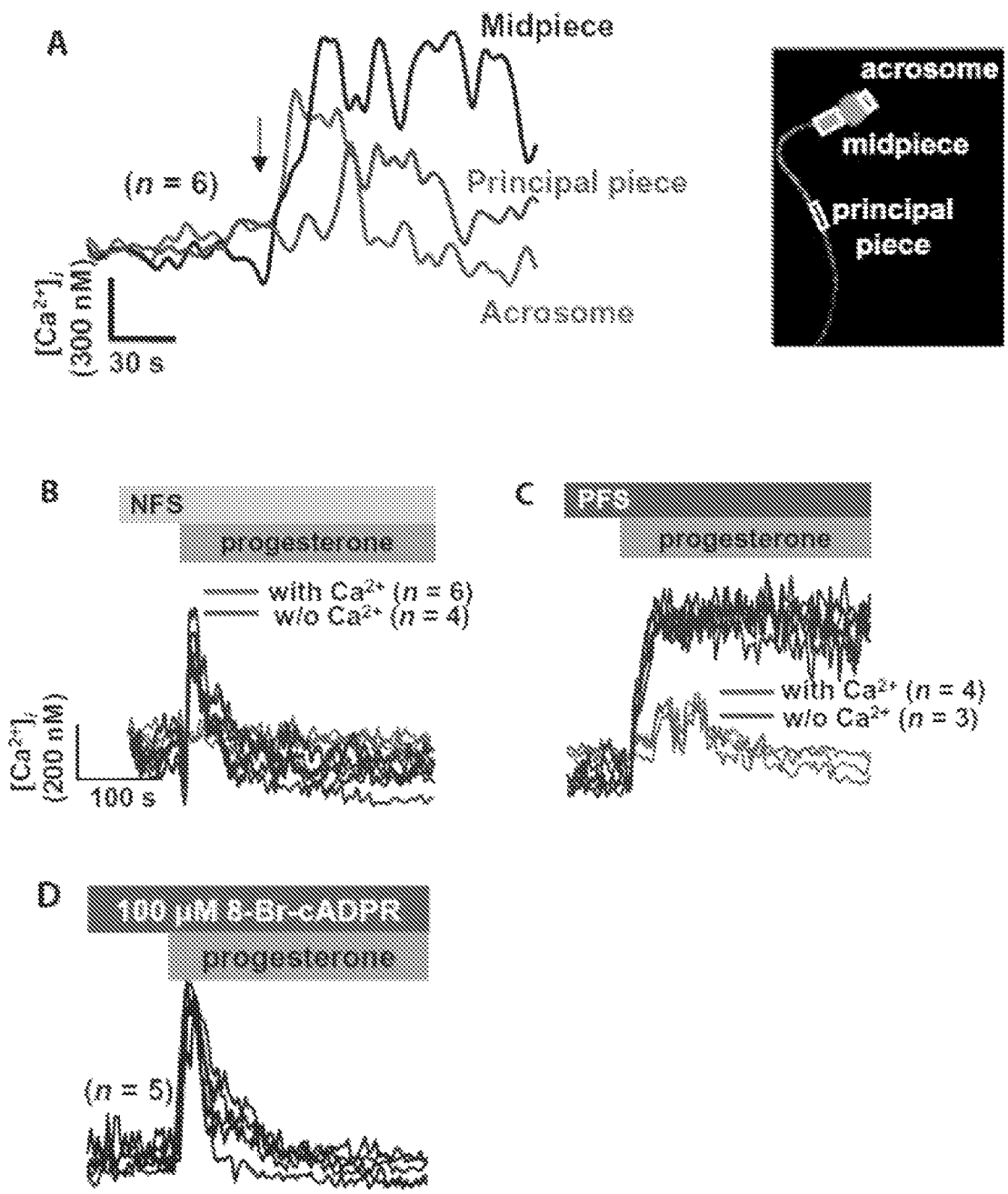
FIG. 2 shows the results of analyzing intracellular calcium changes in prostasome-bound sperm or prostasome-unbound sperm.

As a result, in the prostasome-bound sperm, intracellular calcium release immediately occurred by progesterone so that a pattern of a long-lasting calcium was shown, whereas the prostasome-unbound sperm showed an immediate calcium reaction by progesterone, but did not a pattern of a continuous increase in calcium. This long-lasting in calcium was calcium-dependent, but when the prostasome-bound sperm was pretreated with 8-br-cADPR (an antagonist of cyclic ADP-ribose) and then treated with progesterone, the pattern of a continuous increase in calcium was inhibited (FIG. 2). In conclusion, it can be considered that the pattern of the continuous increase in calcium in sperm is attributable mainly to cyclic ADP-ribose and that this molecule is attributable to the role of CD38 transferred by the binding of prostasome to sperm.

Example 5

Test for Sperm Motility by Prostasome

Sperm motility was measured using a CASA (computer assisted sperm analysis) system (IVOS, Hamilton Thorne Biosciences, USA). The sperm suspension was titrated onto a sperm analysis slide (2X-CEL, Hamilton Thorne Biosciences, USA) having a depth of 20 μm and was automatically photographed using a 4× magnification lens, followed by analysis.

Figure 3:
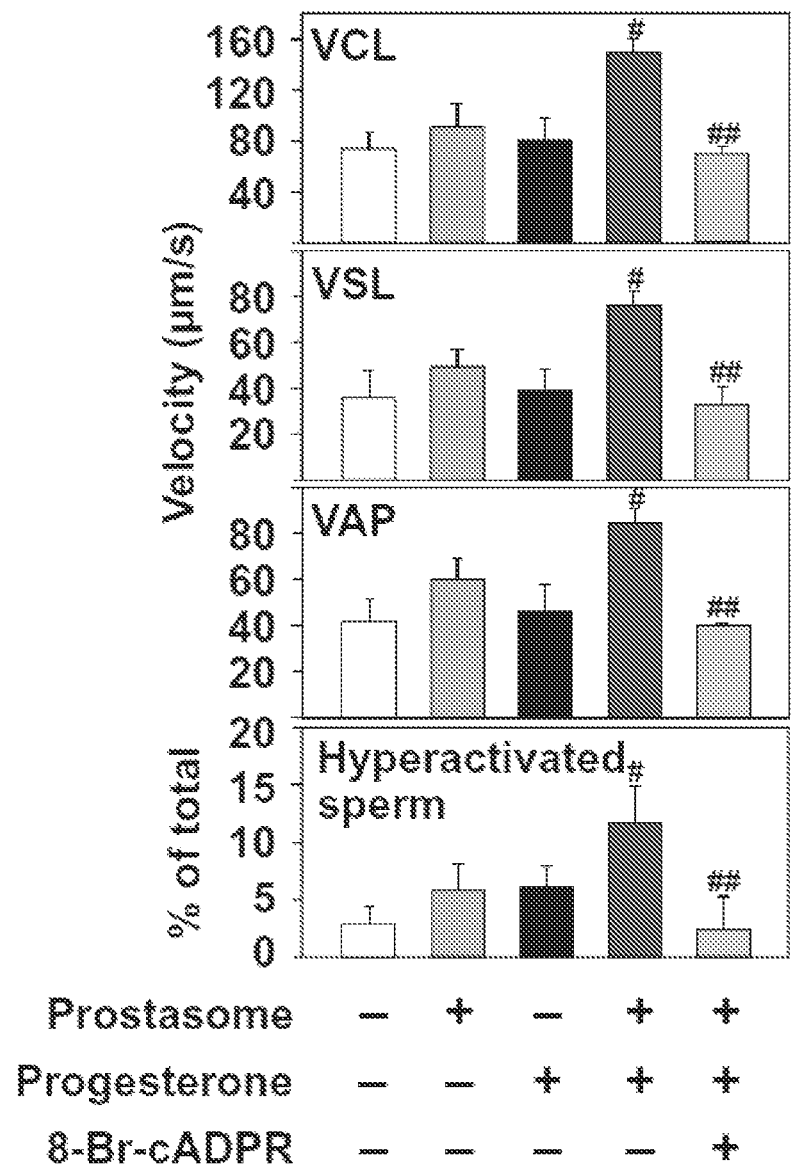
FIG. 3 shows the results of analyzing the change in motility induced by progesterone in prostasome-bound sperm or prostasome-unbound sperm in comparison with a group treated with 8-Br-cADPR that is an antagonist of cyclic ADP-ribose.

As a result, the motility of the prostasome-bound sperm increased within the error range compared to the prostasome-unbound sperm, but was not significant. When the prostasome-bound sperm was treated with progesterone, the motility thereof increased by about 2 times (FIG. 3). Such results could likewise be confirmed from the results of measuring the velocity of curvilinear line (VCL) the velocity of straight-line (VSL), the velocity of average path (VAP) and hyperactivation motility.

Example 6

In Vitro Fertilization Test

In vitro fertilization was performed using a modification of the method of Ren et al. (Ren et al., Nature 413, 603-609 (2001)). 10-12-week-old mice were injected with pregnant mare serum gonadotropin (PMSG) (5 IU; Sigma-Aldrich), and after 48 hours, injected with human chorionic gonadotropin (hCG) (5 IU; Sigma-Aldrich). 14 hours after the final injection, the uterine tube was removed and perfused with IVF medium (Medicult, USA), and the released oocytes were collected using a low-magnification microscope. In order to collect sperm, the epididymis of male mice was removed and cut into small pieces with scissors in the same medium, and swum-out sperm were collected. The number of cells in the sperm was measured, and the sperm were used in the test.

Figure 4:
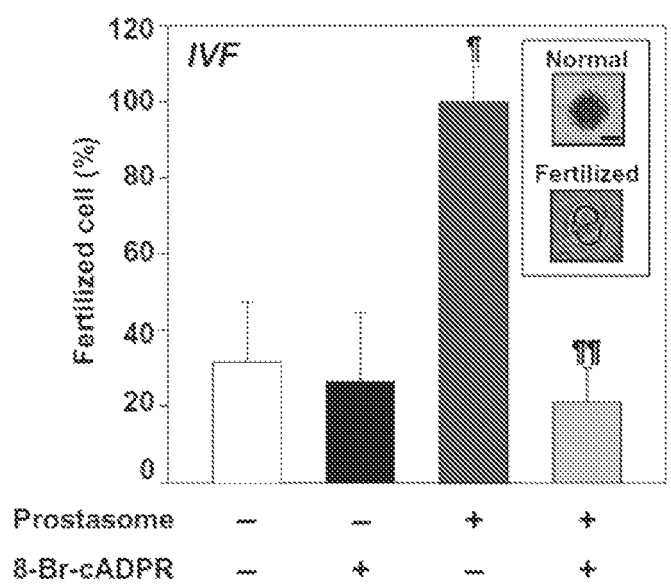
FIG. 4 shows the results of analyzing the change in in vitro fertilization with oocytes in prostasome-bound sperm or prostasome-unbound sperm in comparison with a group treated with 8-Br-cADPR that is an antagonist of cyclic ADP-ribose (inserts: non-fertilized oocyte (upper) and fertilized oocyte (lower)).

As a result, in the case of the prostasome-unbound sperm, the ability to fertilize the mouse oocytes was reduced by about 70% compared to the case of the prostasome-bound sperm. When the sperm were pretreated with 8-Br-cADPR that is an antagonist of cyclic ADP-ribose, the fertilizing ability was reduced by about 70% even in the case of the prostasome-bound sperm. Such results suggest that cyclic ADP-ribose which is formed by CD38 contained in prostasome regulates the function of sperm, thereby determining the fertilizing ability of sperm (FIG. 4).

Example 7

Intrauterine Insemination Test

For intrauterine insemination, ovulation was induced in the same manner as in Example 6. 5 hours after injection of hCG, the abdominal cavity was incised so as to expose the ovary and the uterine tube, each of prostasome-bound sperm and control sperm was injected into the uterine tube of each animal using a catheter. Herein, in order to facilitate the comparison of sperm motility, the location of injection was determined to be a portion close to the uterine cervix so as to provide a space allowing movement to oocytes. 36 hours after the microsurgery, the mice were sacrificed, and the uterine and the uterine tube were removed and perfused with artificial fertilization medium. The total number of oocytes contained in the discharged medium and the number of the cells at the two-cell stage or older in the oocytes were counted, and fertilization rate was calculated using the following equation:

Fertilization rate (%)=number of fertilized embryos at two-cell stage or older÷total number of oocytes× 100

Figure 5:
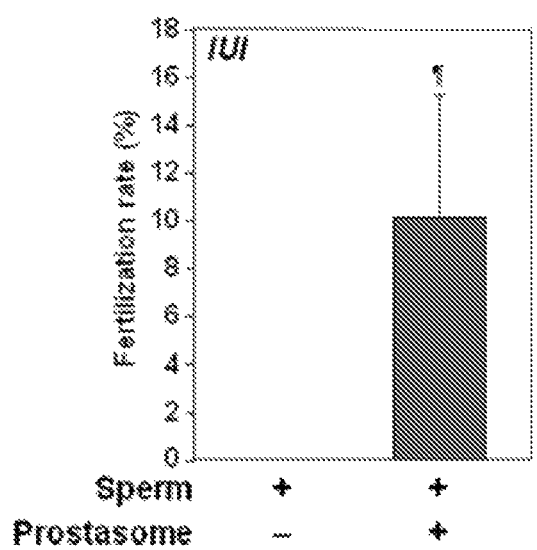
FIG. 5 shows the results of analyzing the change in fertilization with oocytes in the mouse uterus in prostasome-bound sperm or prostasome-unbound sperm.

As a result, the prostasome-bound sperm showed a fertilization rate of about 10% of the total oocytes, but in the case of the prostasome-unbound sperm, no fertilized embryo could be observed (FIG. 5). Such results suggest that cyclic ADP-ribose synthesized by CD38 contained in prostasome transferred to sperm can activate sperm motility even in vivo, thereby increasing the fertilizing ability of sperm.

Example 8

Test for Activation of CD31 in Sperm by CD38

In order to test the activation of CD31 in sperm, the isolated sperm were treated with 600 ng/ml CD38 for each of 0 min, 15 min and 30 min, and then buffer was added thereto to lyse the cells. Also, CD31 antibody was used to perform immunoprecipitation, and Western blot was performed using each antibody in order to examine the phosphorylation of CD31 and to examine interacting proteins.

Figure 6:
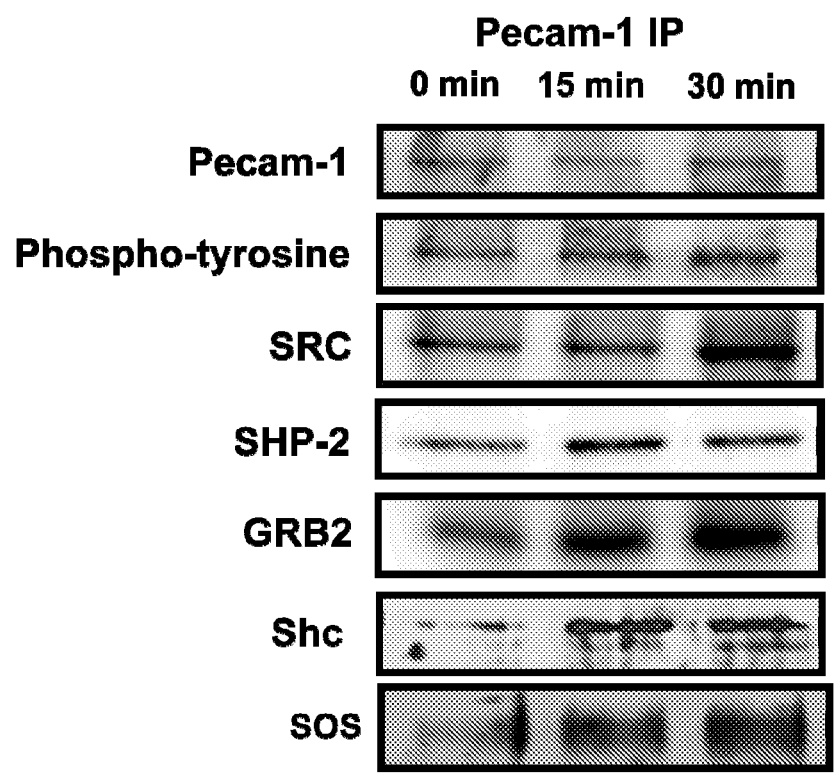
FIG. 6 shows the results of examining the activation of CD31 in sperm treated with CD38 at varying points of time. When sperm was treated with CD38 at varying points of time, the tyrosine phosphorylation of CD31 was increased with time, thus increasing the interaction of CD31 with Src, SHP-2, GRB2, Shc and SOS proteins. This suggests that CD38 increases the phosphorylation of CD31 of sperm so that Src, SHP-2, GRB2, Shc and SOS which are signaling proteins bind to CD31.

As a result, it was seen that the phosphorylation of CD31 increased over time and that Src, SHP-2, GRB2, Shc and SOS as interacting proteins were involved (FIG. 6). Thus, it was believed that signaling for activation of CD31 by stimulation of CD38 would occur through CD31 tyrosine phosphorylation/Src/SHP-2/GRB2/Shc/SOS proteins and that SOS would convert ras-GDP to ras-GTP to activate ERK1/2. In addition, inhibitors of the upstream proteins were used in order to examine whether the proteins are involved in sperm motility and an acrosome reaction.

Example 9

Acrosome Reaction of Sperm by CD38

Figure 7:
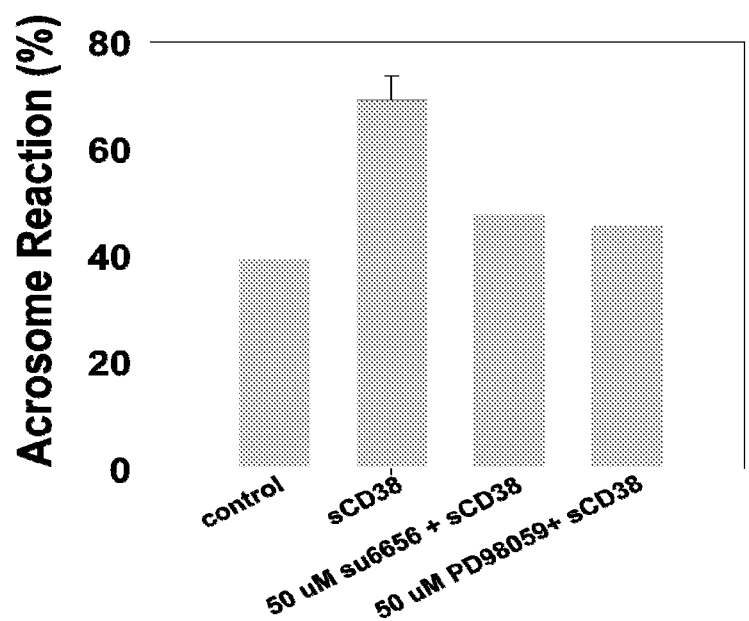
FIG. 7 shows the results of examining whether an acrosome reaction increases when sperm was treated with purified water-soluble CD38 (sCD38). When sperm was treated with water-soluble CD38, the acrosome reaction was significantly increased, and when sperm was treated with a Src inhibitor, a Su6656 and ERK1/2 inhibitor and PD98059 which are the downstream signaling proteins of CD31, the acrosome reaction was inhibited.

To examine the acrosome reaction of sperm, ConA-FITC binding specifically to the acrosome of sperm was used. The isolated sperm were allowed to react with purified CD38 at 37° C. for 2 hours, and then were treated for 40 min with calcium ionophore A23187 that increases calcium in sperm to induce the acrosome reaction of sperm. Then, the sperm were placed on a glass slide, and the acrosome reaction of the sperm was examined with a fluorescence microscope. As a result, the acrosome reaction was significantly increased by CD38 and was inhibited by the Src inhibitor Su6656 and the Erk1/2 inhibitor PD98059 (FIG. 7). This suggests that CD31 is activated by CD38 and involved in the activation of the acrosome reaction by Erk1/2 signaling.

Example 10

Test for Motility of Sperm by CD38

Figure 8:
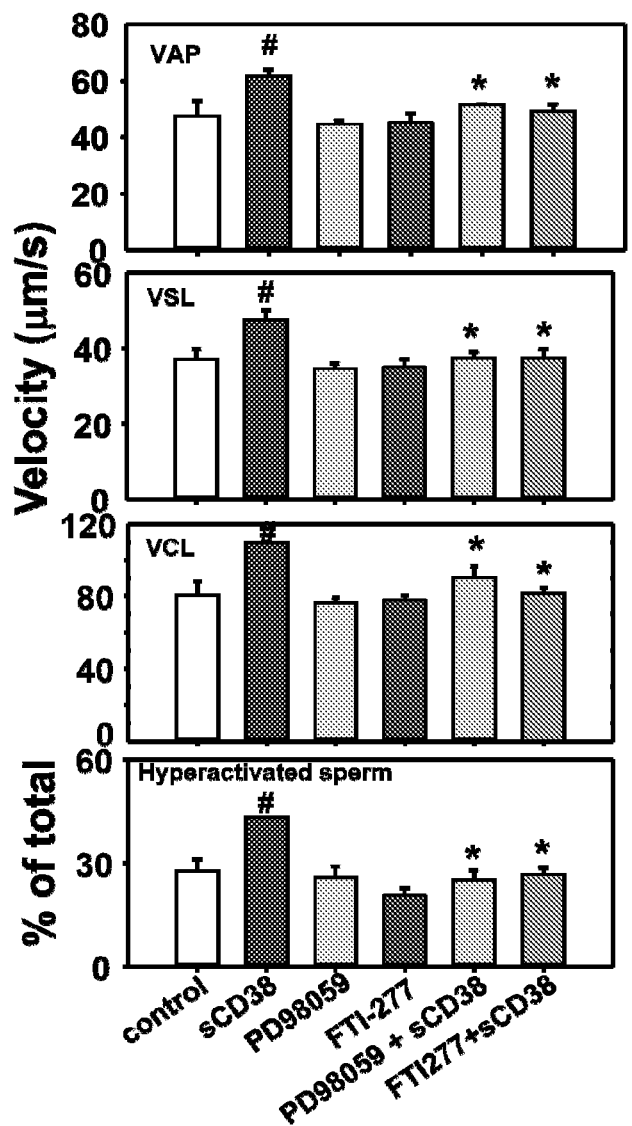
FIG. 8 shows the results of examining changes in sperm motility after treating sperm with purified water-soluble CD38 (sCD38). When sperm was treated with purified water-soluble CD38, sperm motility was increased, and when sperm was treated with an ERK1/2 inhibitor, a PD98059 and ras-GTP inhibitor and FTI-277, sperm motility was inhibited.

The relationship between CD31 activation by CD38 and sperm motility was analyzed. As a result, it was seen that, when sperm were treated with CD38, the motility of the sperm was significantly increased (FIG. 8). Also, it was seen that, when sperm were treated with the ERK1/2 inhibitor PD98059 and the ras-GTP inhibitor (FTI-277) and then treated with CD38, the increase in the motility of the sperm was inhibited. This suggests that the motility of CD31 activated by CD38 was increased by Erk1/2 signaling.

As described above, according to the present invention, the motility of sperm can be regulated using cyclic ADP-ribose, thereby promoting fertilization or inducing contraception as desired.

What is claimed is:
1. A method of facilitating the acrosome reaction and increasing the motility of sperm, the method consisting essentially of contacting the sperm with an effective amount of cyclic ADP-ribose or CD38 purified from prostasome.
2. A method of facilitating the acrosome reaction and increasing the motility of sperm, the method consisting essentially of contacting the sperm with an effective amount of progesterone and an effective amount of cyclic ADP-ribose or CD38 purified from prostasome.
3. The method of claim 1, wherein the sperm is contacted with an effective amount of CD38 purified from prostasome.
4. The method of claim 2, wherein the sperm is contacted with an effective amount of progesterone and an effective amount of CD38 purified from prostasome.

* * * * *